United States Patent [19]

Bodanszky et al.

[11] 4,028,315

[45] June 7, 1977

[54] SOLID PHASE SYNTHESIS OF PEPTIDES

[75] Inventors: Miklos Bodanszky, Shaker Heights, Ohio; John Timothy Sheehan, Middlesex, N.J.

[73] Assignee: E. R. Squibb & Sons, Inc., Princeton, N.J.

[22] Filed: Feb. 20, 1973

[21] Appl. No.: 333,918

Related U.S. Application Data

[60] Division of Ser. No. 81,531, Oct. 16, 1970, Pat. No. 3,743,628, which is a continuation-in-part of Ser. No. 829,127, May 29, 1969, abandoned, which is a continuation-in-part of Ser. No. 559,381, June 22, 1966, abandoned.

[52] U.S. Cl. .................... 260/78 A; 260/112.5 R; 106/197 R
[51] Int. Cl.² ........................................ C08G 69/44
[58] Field of Search ............... 260/112.5, 78 A; 106/197 R

[56] References Cited

UNITED STATES PATENTS

| | | |
|---|---|---|
| 3,216,991 | 11/1965 | Ondetti et al. ............ 260/112.5 |
| 3,645,996 | 2/1972 | Southarel ................. 260/112.5 |
| 3,700,609 | 10/1972 | Tregear et al. ............ 260/112.5 |

FOREIGN PATENTS OR APPLICATIONS 39-18115   8/1964   Japan ........................... 260/112.5

OTHER PUBLICATIONS

Letsinger et al: *J. Am. Chem. Soc.,* 86, 5163–5165 (1964).
Merrifield: *J. Am. Chem. Soc.,* 85, 2149–2154 (1963).
Staab: *Chem. Abstr.,* 53, 16041h (1959).

*Primary Examiner*—Delbert R. Phillips
*Attorney, Agent, or Firm*—Lawrence S. Levinson; Merle J. Smith; Burton Rodney

[57] ABSTRACT

A process for bonding an amino acid to an insoluble hydroxymethyl polymer by esterifying the C-terminal carboxyl group of an N-terminal protected amino acid with the hydroxyl group of an insoluble hydroxymethyl polymer. The esterifying takes place at about room temperature in the presence of a condensing agent. The insoluble hydroxymethyl polymer is a hydroxymethylated copolymer of styrene and divinylbenzene, hydroxymethylcellulose, hydroxymethylated sulfonated polystyrene or polyvinyl alcohol. The condensing agent is dicyclohexylcarbodiimide, carbonyldiimidazole, thionyl chloride, phosphorous oxychloride or ethoxyacetylene. Peptides can be formed by bonding one or more amino acids to the amino acid bonded to the insoluble hydroxymethyl polymer.

6 Claims, No Drawings

SOLID PHASE SYNTHESIS OF PEPTIDES

RELATED APPLICATIONS

The present application is a divisional of copending U.S. application Ser. No. 81,531 filed Oct. 16, 1970, now U.S. Pat. No. 3,743,628 which in turn is a continuation-in-part of U.S. application, Ser. No. 829,127 filed May 29, 1969, now abandoned, which in turn is a continuation-in-part of copending U.S. application Ser. No. 559,381 filed June 22, 1966, now abandoned.

This invention relates to improvements in the solid phase technique of peptide synthesis as well as to novel intermediates in such synthesis.

BACKGROUND OF THE INVENTION

A recent development in the synthesis of peptides is the solid phase technique developed by Merrifield [JACS, 85 2149, (1963)]. In this process, the C-terminal amino acid of the projected peptide, in protected form, is bonded to an insoluble polymer.

This bonding is effected by reacting a chloromethylated polymer in the presence of an organic solvent such as ethanol or ethyl acetate with the triethylammonium salt of the protected amino acid. This reaction takes place at reflux temperature and requires two days to form the desired protected amino acid benzyl ester in maximum yield.

From the ester so formed, the amino protecting group is removed in a manner well known to those skilled in the art, for instance, by treatment with hydrochloric or hydrobromic acid in acetic acid, or with trifluoroacetic acid.

The amino group thereby liberated is acylated with another protected amino acid, and the previous sequence of steps, that is, de-protection and acylation is then repeated until the desired peptide has been attached to the polymer. The peptide is then de-protected and removed from the polymer, e.g., by saponification.

The foregoing process is subject to certain drawbacks; (1) it is necessary to perfrom the esterification step under such relatively drastic conditions that some undesired side reactions, such as racemization of the amino acid is a distinct possibility; (2) an undesirable side reaction, namely the formation of the quaternary ammonium salt from the chloromethyl polymer and triethylamine, occurs during the esterification step; and (3) the conditions required in the esterification step for the attachment of the amino acid peptide to the solid polymeric support are unlike those required in the acylation steps for the attachment of all the remaining amino acids of peptide chain. This difference is a disadvantage in the above method because it precludes the carrying-out of both the esterification and acylation steps in the same reaction vessel, i.e., the method is not totally automated.

DETAILED DESCRIPTION

In accordance with our invention, we have found that an N-terminal protected amino acid can be bonded to an insoluble hydroxymethyl polymer at about room temperature in the presence of a condensing agent. This bonding takes place at essentially the same conditions required for subsequent acylation of the liberated N-terminal amino group by a second amino acid and, if desired, subsequent acylation of the liberated N-terminal amino group of the second amino acid, and so on until the desired peptide chain is built up. Because the conditions are essentially the same, all reactions may be carried out in the same vessel, i.e., the process is totally automated. The insoluble hydroxymethyl polymer can be esterified by simple and well-known procedures such as by reaction with acylamino acid chlorides, mixed anhydrides, or preferably with amino acids in the presence of a condensing agent. Suitable condensing agents include carbodiimides (such as dicyclohexyl carbodiimide), carbonyldiimidazole, thionyl chloride, phosphorus oxychloride and ethoxyacetylene. Of these, dicyclohexyl carbodiimide and carbonyldiimidazole are particularly preferred.

The esterification of the instant invention takes place at essentially the same conditions as those required in the later acylation steps and thus provides a method whereby the entire peptide synthesis may be automated, i.e., all reactions are carried out in the same vessel.

In addition, the esterification of the hydroxymethyl polymer, being effected under relatively mild conditions in a relatively short time, i.e., under 24 hours, and generally not longer than overnight, greatly reduces or eliminates completely the possibility of undesirable side effects, such as the racemization of the amino acid being esterified. Further, the formation of quaternary ammonium salts is precluded.

Polymers which may be employed in the present invention must meet several requirements: (1) that they be insoluble in various solvents employed throughout the synthesis; (2) that they have a stable physical form permitting ready filtration; and (3) that they contain a hydroxymethyl grouping to which the first protected amino acid may be attached by a covalent ester bond.

Examples of such polymers include, but are not limited to, hydroxymethylated copolymers of styrene and divinyl benzene, hydroxymethyl cellulose, polyvinyl alcohol, and hydroxymethylated sulfonated polystyrene.

When a final product having an acid terminal grouping (—COOH) is desired, the use of a polymer having a benzyl alcohol or benzohydrol partial structure such as the hydroxymethylated copolymers of styrene and divinylbenzene is particularly preferred.

The benzene rings contained in such polymers may also be additionally substituted, as for example by negative substituents such as bromo, nitro, cyano and methanesulfonyl groups.

In such a case, the polymer may be removed from the desired peptide sequence, for instance, by treatment with a mixture of hydrogen bromide and either acetic acid or trifluoroacetic acid. If the final product desired would contain a carboxamide or carboxamidine terminal group, then any polymers containing a hydroxymethyl grouping, whether attached to a benzene ring or not, may be employed. Removal of the polymer from the desired peptide sequence in such an instance may be achieved, for instance by treatment with alcoholic ammonia or hydrazine.

In forming peptide sequences of this invention, the amino functions may be protected by commonly used amino protecting groups such as benzyloxycarbonyl, tertiary butyloxycarbonyl, o-nitrophenylsulfenyl, and so forth. Methyl, ethyl, tertiary butyl, benzyl, and so forth may be used to protect carboxyl groups. The hydroxyl protecting groups may be benzyl, tert.-butyl, tetrahydropyranyl and so forth, and the guanidine protecting groups may be nitro, tosyl, p-nitrobenzyloxycarbonyl, protonation, and so forth. A more complete listing of protecting groups may be obtained by reference to standard works on peptide synthesis, e.g., Bodanszky et al., "Peptide Synthesis," chapter 4, Interscience Publishers, 1966, or Schroder et al., "The Peptides," Vol. I, pp. xxiii–xxix, Academic Press, 1965.

The following examples illustrate the present invention without, however, limiting the same thereto. All temperatures are given in degrees Centigrade.

EXAMPLE 1

Acetoxymethyl copolymer (Method A)

Ten grams of 200 to 400 mesh chloromethyl copolystyrene -2% divinylbenzene beads [Biochemistry, 3, 1385 (1965)] containing about 3.4% chlorine/gm. are suspended in 100 ml. ethanol to which 16 ml. acetic acid and 14 ml. triethylamine are added. The suspension is heated while stirring at a bath temperature of 80° C. for 72 hours. After this period, the solvent is decanted and the resin filtered and washed successively with ethanol, acetic acid, and methanol and dried at 60° under vacuum over phosphorus pentoxide. Elementary analysis shows the resin to have chlorine 0.3% and nitrogen 0.6%. An infrared spectrum shows the characteristic bands for carbonyl and carbonoxygen bonds at 5.7 $\mu$ and 8.2 $\mu$ respectively. These are not present in the spectrum of the starting material. A re-treatment of this product for 24 hours at 80° reduces the chlorine and nitrogen content to 0.1 and 0.2%, respectively.

EXAMPLE 2

Acetoxymethyl copolymer (Method B)

A suspension of 30 g. of chloromethylated copolystyrene divinylbenzene in 300 ml. of benzyl alcohol containing 30 g. of potassium acetate is heated with stirring at a bath temperature of 80° for 72 hours. The resin is filtered and washed successively with ethanol, acetic acid, water and methanol and then dried under vacuum at 60° over phosphorus pentoxide overnight. The resin has, on analysis, chlorine 0.3% and nitrogen 0.1%. An infrared spectrum showed the presence of a carbonyl and carbon-oxygen band at 5.8 $\mu$ and 8.2 $\mu$ respectively.

EXAMPLE 3

Hydroxymethyl copolymer

Acetoxymethyl copolymer (8 g.) is suspended in 50 ml. of ammoniacal methanol (5–10 normal) and is stirred at room temperature for 24 hours. The resin is filtered and washed twice with 50 ml. portions of methanol. An infrared spectrum shows the loss of the carbonyl and carbon-oxygen bands present in the spectrum of the starting material.

Analysis: chlorine 0.1%; nitrogen 0.2%.

EXAMPLE 4

Hydroxymethyl copolymer

Acetoxymethyl copolymer (20 g.) is suspended in 200 ml. ethanol, 30 ml. 2N sodium hydroxide added and the mixture heated under reflux for 4 hours. The mixture is diluted with 200 ml. of ethanol and the resin filtered off. It is suspended successively in 200 ml. ethanol; 200 ml. 50% ethanol and 200 ml. double distilled water and filtered. The last two washings are repeated until the filtrate has neutral reaction. The resin is then suspended in and washed with 200 ml. 50% methanol and twice with 200 ml. methanol and sucked dry. It is dried in a vacuum oven at 70° over phosphorus pentoxide, to constant weight. The product weighs 18 g., and its infrared spectrum shows the loss of the carbonyl and carbon-oxygen bands present in the spectrum of the starting material.

EXAMPLE 5

Benzyloxycarbonyl-L-valyl copolymer

Hydroxymethyl copolymer (8 g.) is suspended in 50 ml. of methylene chloride containing 5.0 g. of benzyloxycarbonyl-L-valine. The mixture is stirred for about 20 minutes at room temperature to allow the resin to swell. A solution of 4.0 g. of dicyclohexylcarbodiimide in 10 ml. of methylene chloride is added, and stirring is continued at room temperature for 5 hours. The resin is then filtered and washed successively with methylene chloride, ethanol, acetic acid, methanol, ethyl acetate and methanol. The resin is dried under vacuum at room temperature over phosphorus pentoxide.

Analysis: chlorine 0.1%; nitrogen 0.3%. An infrared spectrum shows carbonyl, carbon-oxygen and carbon-nitrogen bands at 5.8 $\mu$; 8.2 $\mu$ and 6.5 $\mu$. A sample of this preparation is treated with a methanolic solution of ammonia for 40 hours at room temperature. The resin is filtered and washed twice with 25 ml. portions of methanol. The filtrate and washings are combined and the solvent evaporated in vacuo. From the residue benzyloxycarbonyl-L-valine amide (m.p. 206° C.) and benzyloxycarbonyl-L-valine methyl ester (m.p. 54°–56° C.) are obtained. The infrared spectrum of the recovered treated resin shows no carbonyl, ester or carbon-nitrogen bands.

EXAMPLE 6 t-Butyloxycarbonyl-L-valyl copolymer t-Butyloxycarbonyl-L-valine (2.2 g.) is added to a solution of 1.65 g. of N,N'-carbonyldiimidazole in 10 ml. of methylene chloride and the resulting solution stirred for one-half hour at room temperature, when the evolution of carbon dioxide has ceased. To this solution then 5 g. of hydroxymethyl copolymer and 30 ml. of methylene chloride are added and the suspension stirred overnight at room temperature. The resin is then filtered and washed successively with methylene chloride, ethanol, acetic acid and methanol and finally dried at room temperature in vacuum over phosphorus pentoxide. Analysis: nitrogen 0.5%; chlorine 0.1%, indicating 0.3 mm ester/gm. of resin. An infrared spectrum shows carbonyl, carbon-oxygen and carbon-nitrogen bands at 5.8 $\mu$; 8.2 $\mu$ and 6.5 $\mu$ which are not present in the spectrum of the hydroxymethyl copolymer.

EXAMPLE 7 t-Butyloxycarbonyl-S-benzyl-L-cysteine copolymer t-Butyloxycarbonyl-S-benzyl-L-cysteine (3.1 g) is added to a solution of 1.65 g. of N,N'-carbonyldiimidazole in 10 ml. of methylene chloride and the solution formed stirred for one-half hour at room temperature. To this solution 7 g. of hydroxymethyl copolymer and an additional 30 ml. of methylene chloride are added and the suspension stirred overnight at room temperature. The solvent is decanted and the resin washed successively with methylene chloride, ethanol, acetic acid and methanol and finally dried at room temperature in vacuum over phosphorus pentoxide. The product weighs 8.1 g. indicating the presence of 0.5 mm ester/gm. of resin. An infrared spectrum shows carbonyl, carbon-oxygen and carbon-nitrogen bands at 5.8 $\mu$; 8.2 $\mu$ and 6.5 $\mu$ and is indistinguishable from an infrared spectrum of t-butyloxycarbonyl-S-benzyl-L-cysteine copolymer prepared in the conventional manner.

EXAMPLE 8 t-Butyloxycarbonyl-L-proline polyvinyl alcohol polymer

Following the procedure of Example 6 but employing t-butyloxycarbonyl-L-proline as the amino acid and polyvinyl alcohol as the insoluble polymer, the title product is obtained.

EXAMPLE 9 t-Butyloxycarbonyl-L-phenylalanine sulfonated polystyrene polymer

Following the procedure of Example 6 but employing t-butyloxycarbonyl-L-phenylalanine as the amino acid and hydroxymethylated sulfonated polystyrene as the insoluble polymer, the title product is obtained.

EXAMPLE 10 t-Butyloxycarbonyl-O-benzyl-L-serine hydroxymethylcellulose polymer

Following the procedure of Example 6 but employing t-butyloxycarbonyl-O-benzyl-L-serine as the amino acid and hydroxymethylcellulose as the insoluble polymer, the title product is obtained.

What is claimed is:

1. A process for bonding an amino acid to an insoluble hydroxymethyl polymer comprising esterifying the C-terminal carboxyl group of an N-terminal protected amino acid with the hydroxyl group of an insoluble hydroxymethyl polymer selected from the group consisting of hydroxymethylated copolymers of styrene and divinylbenzene, hydroxymethylcellulose, hydroxymethylated sulfonated polystyrene and polyvinylalcohol, the esterifying taking place at about room temperature in the presence of a condensing agent selected from the group consisting of dicylcohexylcarbodiimide, carbonyldiimidazole, thionyl chloride, phosphorous oxychloride, and ethoxyacetylene.

2. A process according to claim 1 hwerein the condensing agent is dicyclohexylcarbodiimide.

3. A process according to claim 1 wherein the hydroxymethyl polymer is a hydroxymethylated copolymer of styrene and divinylbenzene.

4. A process according to claim 3 wherein the condensing agent is dicyclohexylcarbodiimide.

5. A process for preparing a peptide comprising bonding an N-terminal protected amino acid to an insoluble hydroxymethyl polymer according to claim 1, deprotecting the amino acid, and acylating the liberated amino group with the free carboxyl group of an N-terminal protected amino acid, the acylating taking place at about room temperature in the presence of a condensing agent selected from the group consisting of dicyclohexylcarbodiimide, carbonyldiimidazole, thionyl chloride, phosphorous oxychloride, and ethoxyacetylene.

6. A process according to claim 3 wherein the condensing agent is carbonyldiimidazole.

* * * * *